(12) United States Patent
Alperin

(10) Patent No.: US 6,245,027 B1
(45) Date of Patent: Jun. 12, 2001

(54) METHOD OF MEASURING INTRACRANIAL PRESSURE

(76) Inventor: Noam Alperin, 2853 N. Wolcott Unit B, Chicago, IL (US) 60657

( * ) Notice: Subject to any disclaimer, the term of this patent is extended or adjusted under 35 U.S.C. 154(b) by 0 days.

(21) Appl. No.: 09/399,566

(22) Filed: Sep. 20, 1999

Related U.S. Application Data

(63) Continuation-in-part of application No. 09/058,484, filed on Apr. 10, 1998, now Pat. No. 5,993,398.

(51) Int. Cl.$^7$ ........................................ A61B 5/00
(52) U.S. Cl. ............................................. 600/561
(58) Field of Search ........................ 600/437, 454, 600/458, 465, 561

(56) References Cited

U.S. PATENT DOCUMENTS

| | | | |
|---|---|---|---|
| 4,276,885 | * 7/1981 | Tickner | 600/437 |
| 4,689,560 | * 8/1987 | Nayler et al. | 324/306 |
| 5,257,625 | * 11/1993 | Pelc | 600/410 |
| 5,895,358 | * 4/1999 | Becker et al. | 600/454 |

* cited by examiner

Primary Examiner—Eric F. Winakur
Assistant Examiner—Pamela L. Wingood
(74) Attorney, Agent, or Firm—Welsh & Katz, Ltd.

(57) ABSTRACT

A method and apparatus are provided for finding a fluid conduit of a human body within a set of images collected over a portion of a cardiac cycle and where each image of the set of images is formed by a plurality of image elements. The method includes the steps of selecting a reference image element within the fluid conduit from the plurality of image elements, determining a velocity profile of each of the image elements over the cardiac cycle and identifying the fluid conduit by correlating the velocity profile of the reference element with velocity profiles at least some of the other image elements.

36 Claims, 20 Drawing Sheets

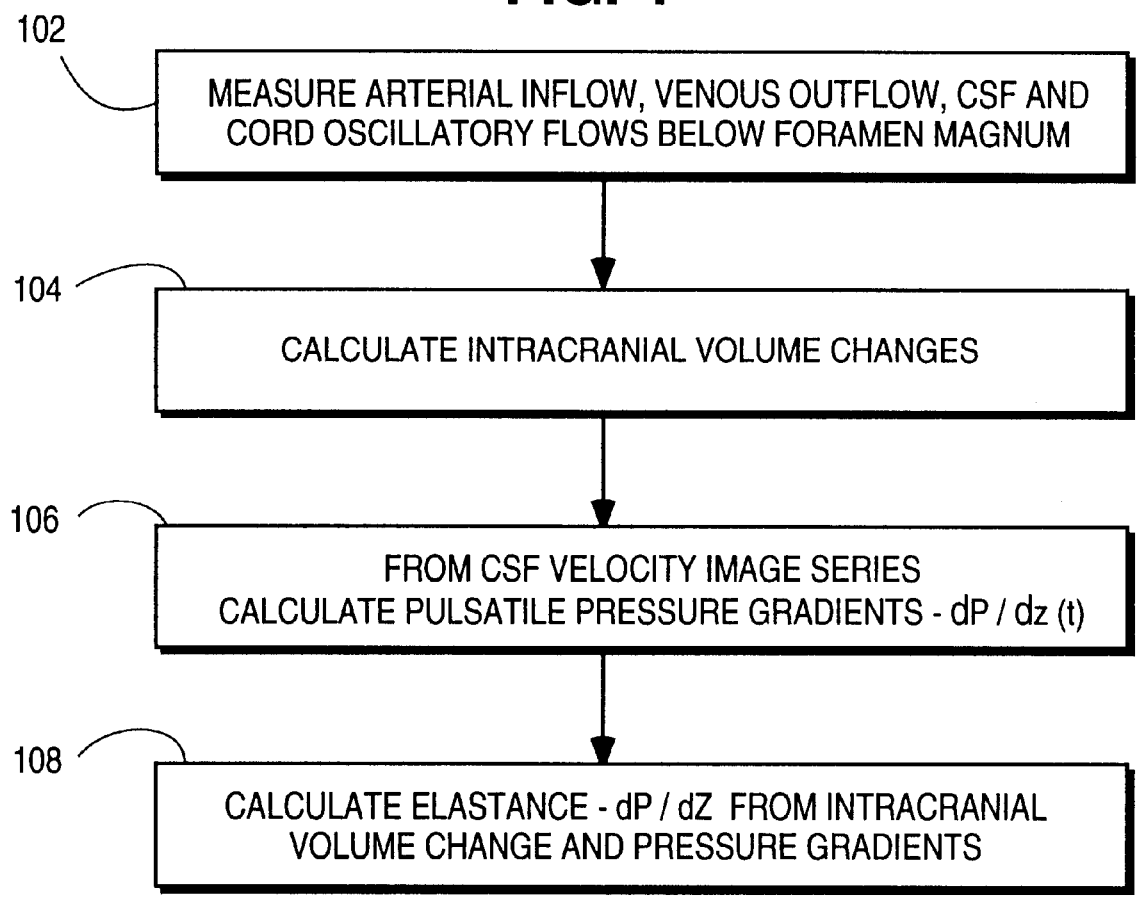

ARTERIAL AND JUGULAR BLOOD VOLUMETRIC FLOW WAVEFORM

CSF VOLUMETRIC FLOW WAVEFORM

CORD MOVEMENT WAVEFORM

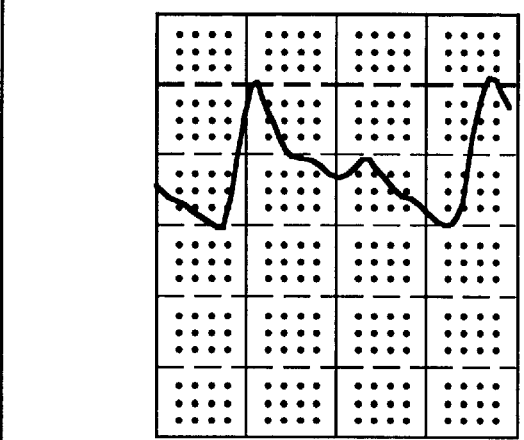
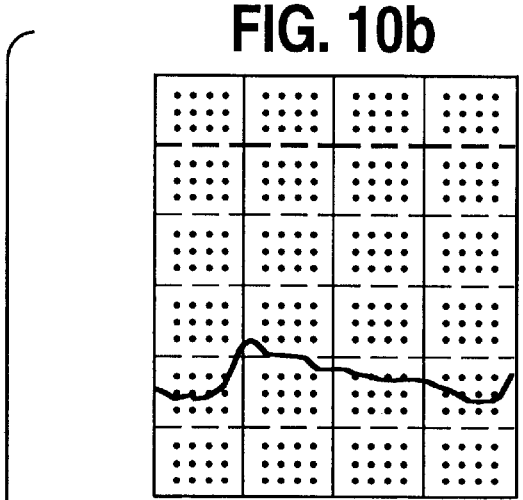
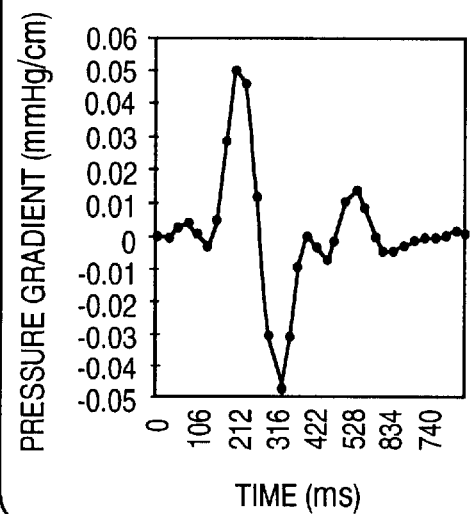
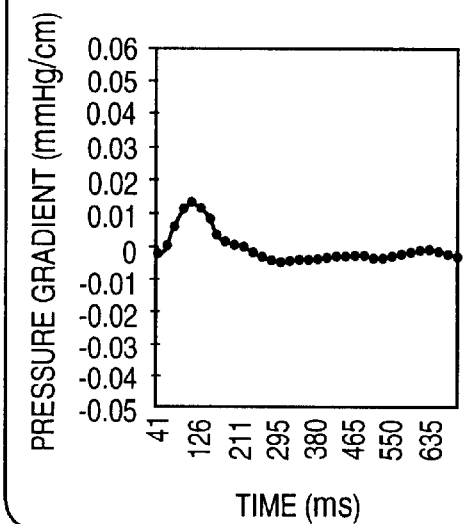
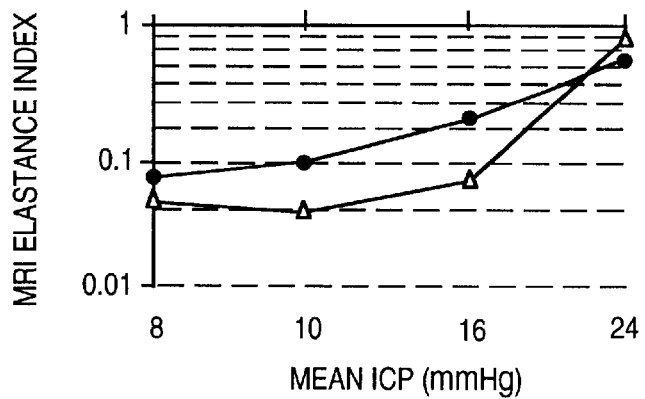

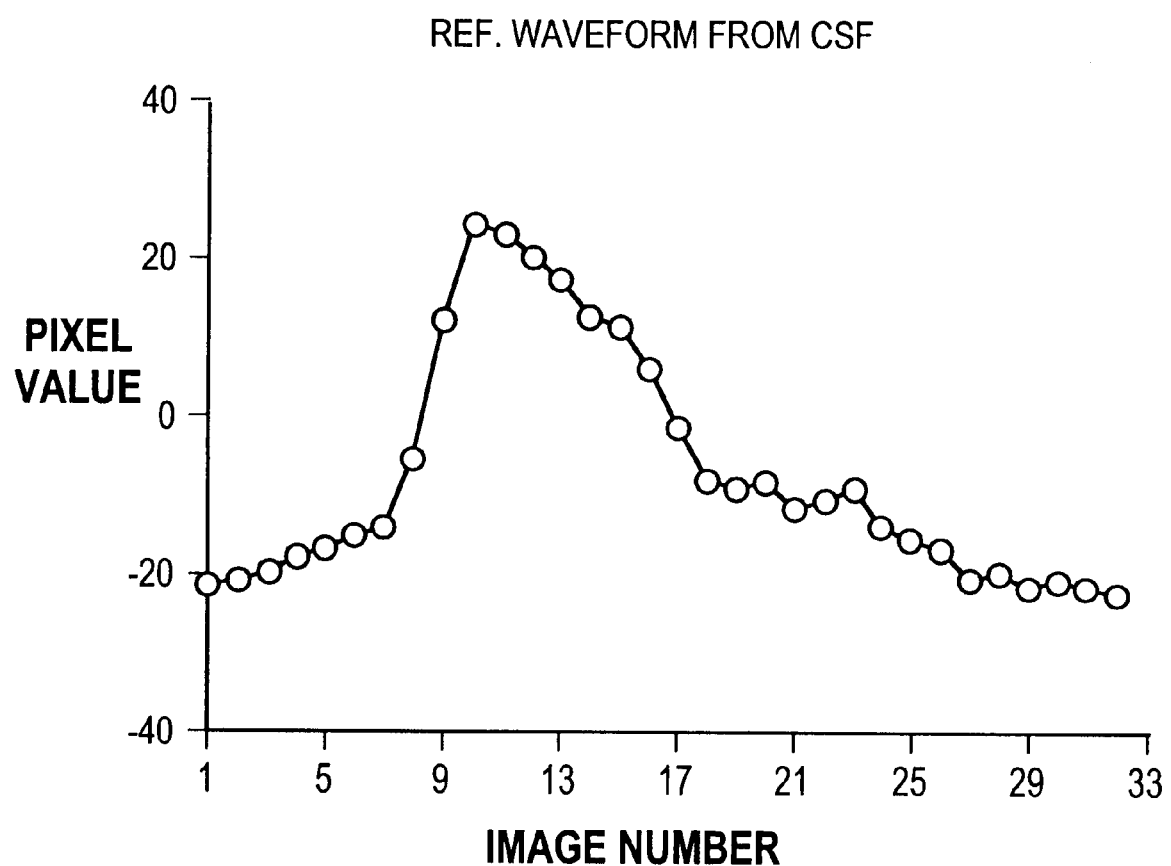

METHOD OF MEASURING INTRACRANIAL PRESSURE

This application is a CIP of application Ser. No. 09/058,484 filed Apr. 10, 1998, now U.S. Pat. No. 5,993,398.

FIELD OF THE INVENTION

The field of the invention relates to medical diagnostic testing and more particularly to methods of measuring intracranial pressure within the cranium of a patient.

BACKGROUND OF THE INVENTION

Intracranial pressure (ICP) and compliance are important clinical parameters for diagnosis and treatment of diseases of the central nervous system (CNS). Elevated intracranial pressure, if left untreated, may result in patient death or permanent damage. Techniques currently available to measure ICP are invasive and associated with risk. In addition, penetration into the CNS space to measure the ICP often alters the pressure.

In a closed system, such as the cranium, the inside pressure and volume are related. The change in pressure due to change in volume is determined by the overall mechanical elastance of the system. Studies of the relation between intracranial volume and pressure date back almost 200 years. In 1873, Alexander Monro stated that the intracranial space contains two compartments (brain matter and blood) that can change in volume. Since neither can be compressed and the cranium is rigid, he concluded that the volume of blood within the intracranial space is constant. Sixty years later, in light of the discovery of the CSF by Magendi, Burrows concluded that intracranial blood volume does change and it is accompanied by a reciprocal change in the volume of the other two compartments, brain and CSF. This is known as the Monro-Kelli doctrine. The majority of the added volume during systole is accommodated by displacement of the CSF into the spinal canal.

Ryder and others injected fluid into the CNS space to find the relation between the intracranial pressure and volume. The derived pressure-volume curve, also called the elastance curve, is well described by a monoexponential curve. The elastance (inverse of compliance) is defined as the change in pressure due to a change in volume (dP/dV). The intracranial elastance (i.e., the derivative of the pressure-volume curve) is therefore also an exponential function of the intracranial volume.

The most practical method of assessing the volume-pressure relationship is the volume pressure test. In this test, the total volume of the system is rapidly loaded by injection of a uniform amount of fluid into the lateral vertical. The pressure change resulting from the volume loading is termed volume-pressure response (VPR).

In both clinical patients and experimental animals, the relationship between VPR and ICP has been shown to be linear. This linear relation validates the monoexponential volume-pressure relation. The elastance coefficient (the coefficient defining the shape of the volume-pressure exponential curve) is determined from the slope of the VPR-ICP linear relationship. The intracranial compliance coefficient is the reciprocal of the elastance coefficient.

In clinical practice, intracranial pressure is often measured for the diagnosis and clinical management of closed-head injuries such as trauma and intracranial bleeding or of chronic disorders such as hydrocephalus, malformations involving hindbrain herniation and pseudotumor cerebri. Intracranial pressure measurement is an invasive procedure and thus it is associated with risk.

Our non-invasive method for measurement of the intracranial pressure, described below under illustrated embodiments of the invention, utilizes measurements of the pulsatile blood and CSF volumetric flow rates (see FIGS. 2 and 3, items 40, 42, 44, 46, 48 and FIG. 5). In general, the lumen of the flow conduit has to be delineated in order to calculate the flow rate. A number of past efforts have been reported which have been directed to this problem. These efforts have been only partially successful.

For example, Burdart et. al. developed an automated segmentation technique for phase contrast MRI images using pixel intensity differences between vessel and background within a single image. Using the fact that pixels have either positive or negative intensity magnitudes depending on their direction (whereas stationary pixels have intensity value significantly closer to zero) the vessels were threshold against a pre-selected threshold index. Hu et. al. used a region growing technique with an intensity threshold to segment the entire vascular structure in a set of three-dimensional MRI images of blood vessels. Singleton and Pohost extended the region growing technique to segment cardiac lumens using a region growing method, along with eroding and dilating operations, to include holes and excluding isolated regions outside the ventricle. Baledent et. al. segmented CSF flow area in phase contrast MRI technique using the fundamental frequency component, obtained from Fast Fourier Transform to enhance the pulsatile dynamics.

Cross-correlation technique has also been used, as an image processing technique for applications not related to segmentation of flow regions. Bandettini et. al. used cross-correlation between a reference pattern and image intensity values in echo-planar MR images that were acquired during brain stimulation. Regions in which signal intensity changes correlated with the activation pattern were identified as the active region in the brain. A arbitrary threshold value was used to differentiate between activated and background regions.

The ability to automate the identification of the lumen's borders for quantification of volumetric flow measurements would make the results more reproducible and reliable and less dependent on the skills of the operator. With automated blood and CSF flow measurements, ICP measurements will become more reliable. Therefore there is a need to automate identification of the lumen borders for quantification of pulsatile CSF and blood flow rates.

BRIEF DESCRIPTION OF THE DRAWINGS

FIG. 4 is a flow chart of the method of the system of FIG. 1;

FIGS. 10a–b depicts further pressure gradient results derived by the apparatus of FIG. 1;

FIG. 11 depicts comparative results of the apparatus of FIG. 1 and invasive intracranial pressure measurements over a wide range of mean ICP in four patients;

FIG. 16B depicts a velocity versus time waveform for the location of the reference picture element of FIG. 16A;

SUMMARY

A method and apparatus are provided for finding a fluid conduit of a human body within a set of images collected over a portion of a cardiac cycle and where each image of the set of images is formed by a plurality of image elements. The method includes the steps of selecting a reference image element within the fluid conduit from the plurality of image elements, determining a velocity profile of each of the image elements over the cardiac cycle and identifying the fluid conduit by correlating the velocity profile of the reference element with velocity profiles at least some of the other image elements.

DETAILED DESCRIPTION OF A PREFERRED EMBODIMENT

Figure 1:
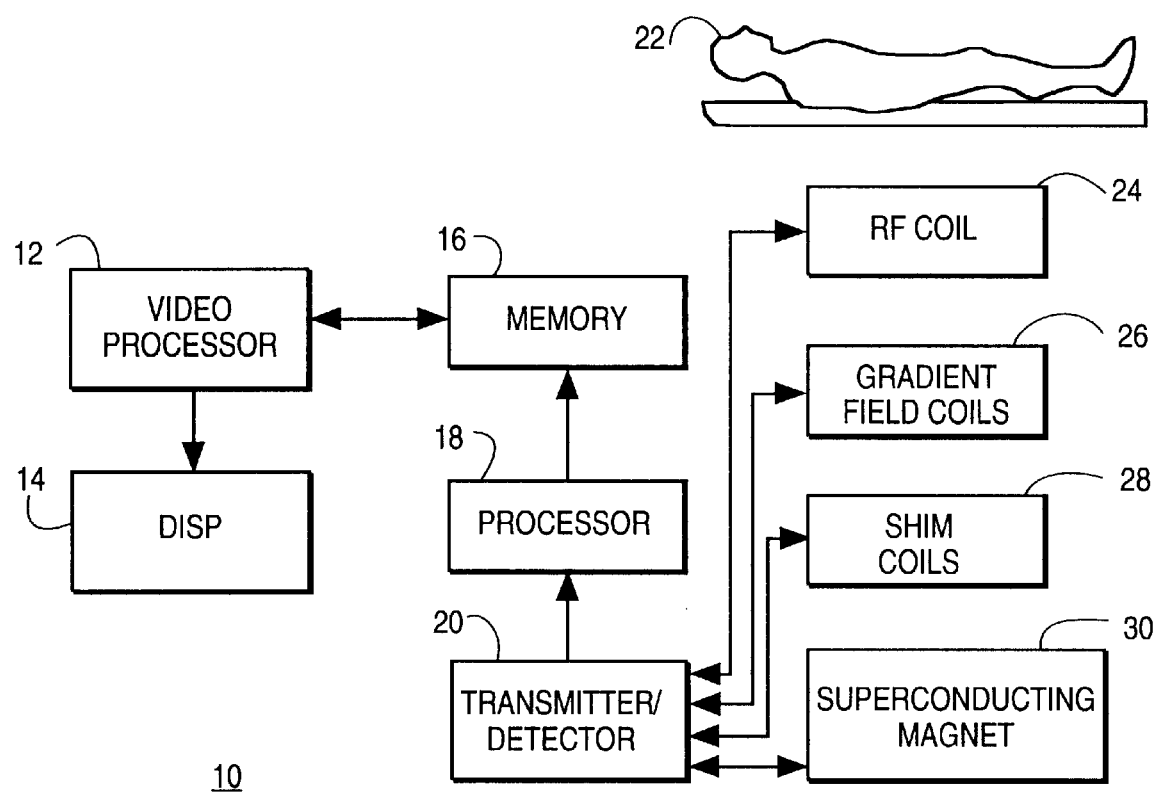
FIG. 1 is a block diagram of apparatus for calculating intracranial pressure in accordance with an embodiment of the invention.

FIG. 1 is a block diagram of a device 10 that may be used to determine intracranial pressure (ICP) non-invasively. Under the embodiment, magnetic resonance imaging (MRI) techniques are used to determine ICP from a series of measurements performed on a subject. The MRI imaging techniques may be used to obtain flow data regarding transcranial (i.e., into and out of the cranium) blood, cranial spinal fluid flow and spinal cord oscillatory movement. The imaging techniques may also be used to obtain data regarding the conduits within which the measured flows occur. Together, the measured values may be used to determine a value of intracranial pressure.

To obtain flow data, an MRI imaging system 10 (e.g., a G.E. Signa 1.5 T) may be set up to measure velocity information at each point (voxel) in three-dimensional space. As is well known in the art, a MRI system 10 may be provided with a superconducting magnet 30, gradient field coils 26 and shim coils 28 to create a varying magnetic field throughout an space (e.g., within the cranium of a patient). The superconducting magnet 30 and gradient field and shim coils 26, 28 provide a varying magnetic field of a known magnitude and variance throughout the measured space. The magnetic field causes atoms (e.g., protons) to align themselves to the magnetic field in a known manner.

A series of radio frequency pulses may be applied to the space at a Larmor frequency of the selected atoms within a selected space. Since the Larmor frequency of the atoms vary as a function of the magnetic field which the atoms experience, only a few atoms at known locations will resonate and generate a measurable signal during a free induction decay (FID) of the electrons of those atoms. A velocity of an atom may be determined by a phase shift of the signal from the selected atoms caused by the movement of the atom within a magnetic field gradient.

By selecting the proper magnetic field and Larmor frequency, a slice of tissue of a subject 22 may be examined in three-dimensional space. Further, since velocity can be determined at any point (area) along the slice of tissue based upon phase shifts, flow through vascular structures (e.g., arteries, veins, etc.) can be determined by integrating and averaging velocity through the selected areas. Determination of flow then becomes the simple step of multiplying velocity times area.

Based upon transcranial fluid flows of a subject, ICP may be determined based upon a set of flow measurement steps, and associated calculations. FIG. 4 is a flow chart 100 which depicts a series of steps that may be used in determining ICP. Reference will be made to FIG. 4 as appropriate to an understanding of the invention.

As a first step 102, flow of blood into and out of the cranium, may be determined. Blood flow into the cranium is pulsatile. Also, at each instant the value of blood flow into the cranium is not equal to blood flow out of the cranium. However, over the cardiac cycle the integral of blood flow into the cranium is equal to the integral of blood flow out of the cranium except for a very small amount of blood plasma that may be converted into CSF during this cycle. Venous outflow is composed mainly of jugular flow and a small amount of flow that may go through other channels such as the ophthalmic veins. The flow through the other channels is estimated from the constraint that over a cardiac cycle inflow equals outflow. The flow through the jugular is measured directly under the process described herein. Not measuring the flow in those other channels doesn't adversely affect ICP results. Stated differently, net arterial inflow does not equal net jugular flow but does equal venous flow that can be calculated from the measured jugular flow.

During each systolic portion of the cardiac cycle, a volume of blood is pumped into the brain through the associated arteries. A delay occurs before an equal amount of blood perfuses through the brain and exits the cranium through the veins. Since blood is incompressible, the differences in volume is, for the most part, accommodated by movement of the cranial spinal fluid and movement of the spinal cord within the spinal column (spinal cord oscillatory flow). The majority of the added volume in the cranium is accommodated in the spinal compartment in the form of displaced CSF, especially at lower levels of increased ICP.

The differences provide a means of determining ICP. To determine ICP, an instantaneous change in the volume of the intracranial content is calculated according to the equation as follows:

$$I(t)=A(t)-V(t)-CSF(t)-\text{Cord}(t),$$

where $A(t)$ is the total arterial flow, $V(t)$ is the total venous flow (the sum of the measured jugular flow and the estimated other venous flow), $CSF(t)$ is the rate of CSF outflow through the foramen magnum and $\text{Cord}(t)$ is the volumetric rate of spinal cord displacement. More specifically, $I(t)$ can be defined to be the portion of the time-varying arterio-venous flow which is not compensated by the CSF and spinal cord displacement. The integral of $I(t)$ is the time-varying intracranial volume change from which the systolic intracranial volume change may be derived. Time-varying flow rate waveforms may be derived from the MRI phase images by integration of phase values representing the velocities inside regions of interest defining the area of the vessels, the cord and the CSF space.

Figure 5A:
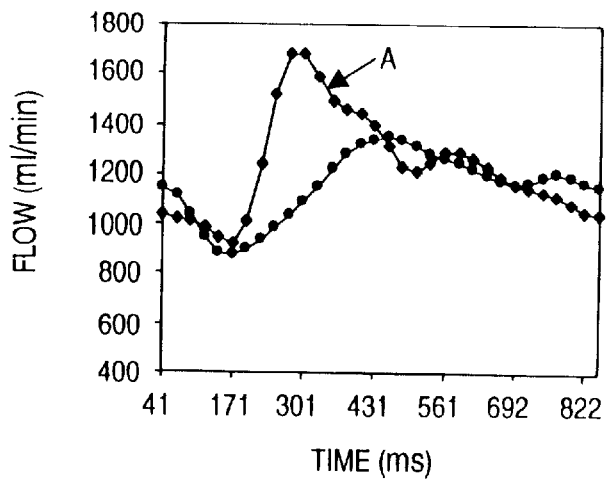
FIGS. 5a–c depicts the time course of arterial and jugular volume flow, CSF and cord flows measured by the apparatus of FIG. 1.
Figure 5B:
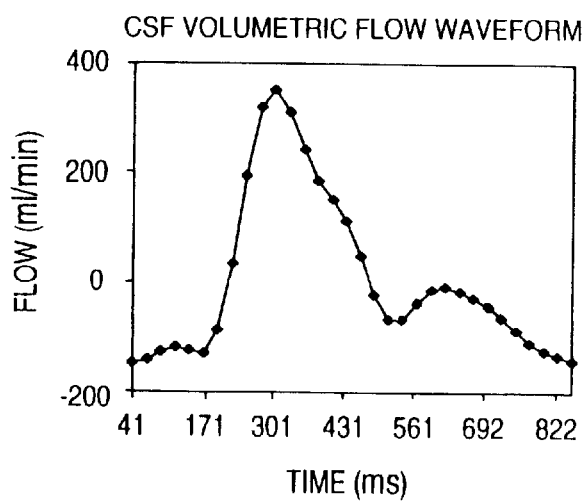
Figure 5C:
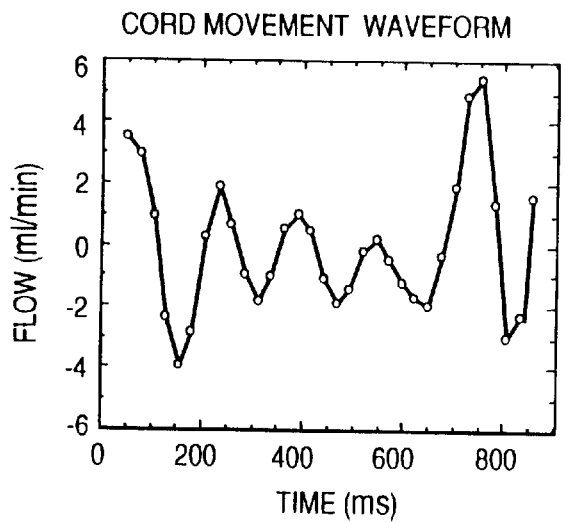

As indicated, the intracranial volume change during the cardiac cycle may be calculated from the time-varying net flow into and out of the cranium. FIGS. 5a–c provides an example of measured data regarding blood flow, cranial spinal fluid flow and cord movement.

Arterial blood inflow and venous outflow may be measured during a first scan using the well-known MRI technique that is optimized for quantification of blood flow. CSF and cord displacement below the foramen magnum may be measured during a second MRI scan that is optimized for slow flow. The two scans are performed in quick succession, at an axial location below the foramen magnum. Blood flow through the four major arteries (two internal carotid and two vertebral) and two veins (jugular) is obtained from one dynamic scan. An example of an MRI phase image representing flow in the major blood vessels is shown in FIG. 2.

Figure 3A:
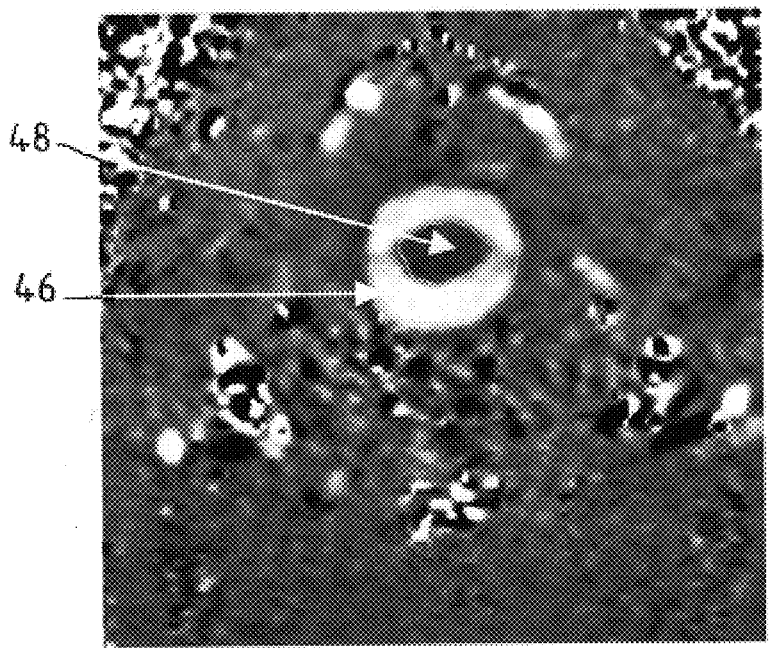
FIGS. 3a–b depicts cranial-spinal fluid and spinal cord images collected by the apparatus of FIG. 1.
Figure 3B:
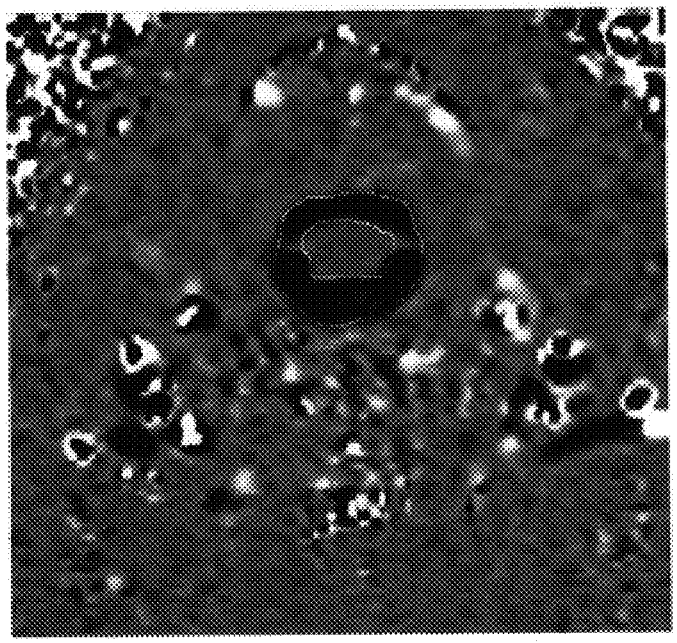

The second scan may be used to measure cervical CSF and cord pulsation. An example of MRI phase images of the CSF flow taken at different cardiac phases are shown in FIGS. 3a–b. In each case, a section 5 mm thick, with a field of view of 1–16 cm, a matrix size of 256×160 mm and two averages may be used. The shortest possible repetition time TR (e.g., 21–26 ms) may be used to optimize temporal resolution (equal to twice the TR). A high velocity encoding (e.g., 80 cm/sec) with flip angle of 20–30 degrees may be used for measurement of blood flow, and a low velocity encoding (e.g., 3–10 cm/sec) with flip angle of 20 degrees may be used for measurements of CSF flow and cord motion. In all scans, the maximum number of time points allowed per cardiac cycle (e.g., 32) may be selected to minimize errors due to interpolation and resampling.

Figure 2:
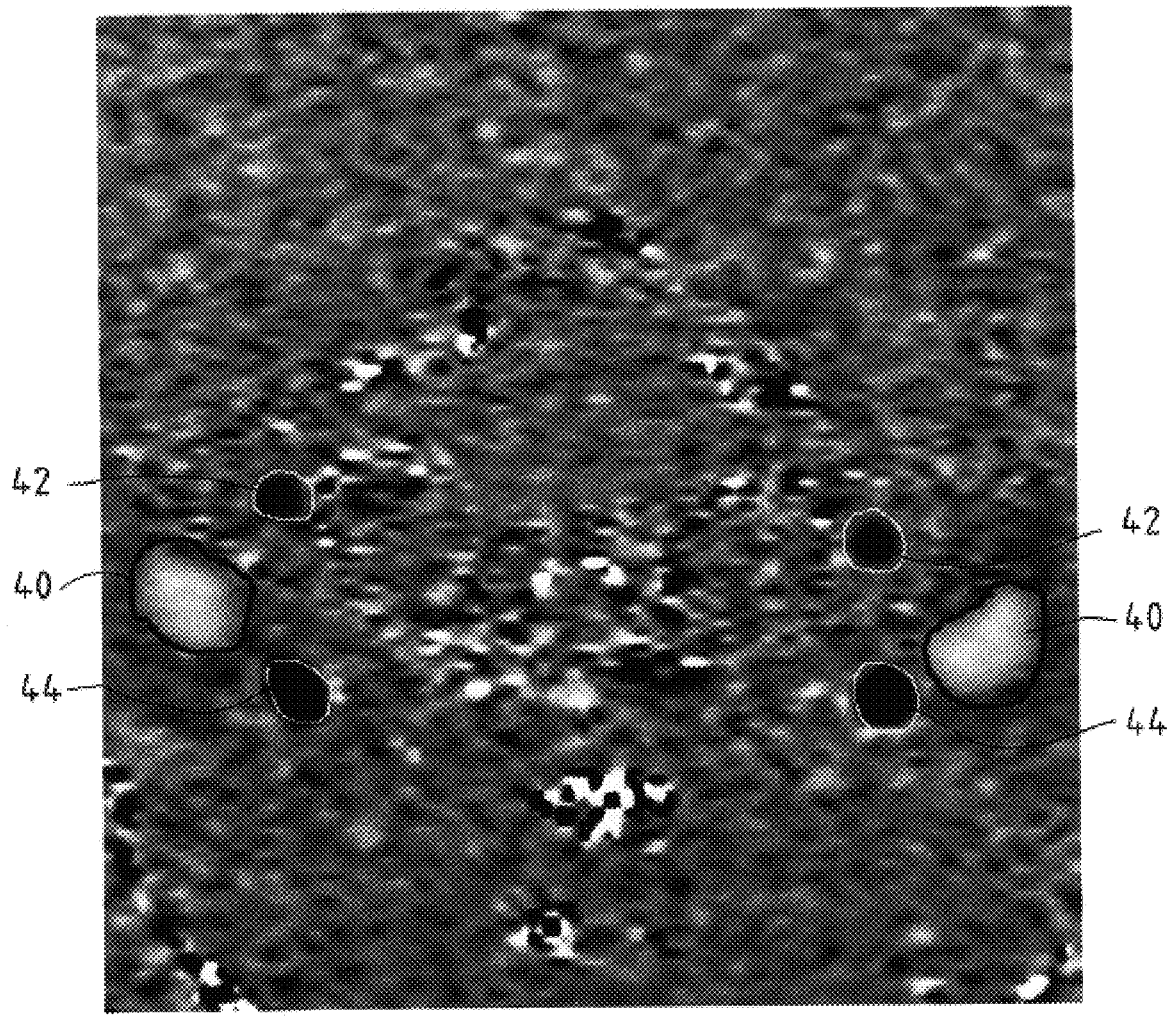
FIG. 2 depicts a blood flow image collected by the apparatus of FIG. 1.

Within FIG. 2 the dark areas 42, 44 depict blood flow into the cranium through the carotid and cerebral arteries. The light areas 40 depicts blood flow out of the cranium through the jugular veins.

To determine a net blood flow, the blood flow within the arteries 42, 44 and veins 40 may each be determined. First the size (e.g., in number of pixels) of each artery and vein may be determined. The number of pixels making up each artery and vein may be determined (marked) by edge-detecting software, or by manually marking the appropriate areas 40, 42, 44 (e.g., by clicking on the appropriate areas with a computer mouse).

Next, a velocity may be determined within each artery and vein. Since the pixel values within the marked areas are a measure of velocity, the velocity values of each pixel within each marked area may be integrated. The integrated velocity may be averaged to determine an average blood flow within the vein or artery.

Finally, the net blood flow may be determined. To determine flow in each vein and artery 40, 42, 44 the average velocities may be multiplied by the areas.

It should be noted, that the determination of net blood flow may be determined in terms of instantaneous values. Each scan may be used to provide a size of each vein and artery, as well as an average velocity and blood flow in that vein or artery for that scan. The result of a series of scans may be a profile of blood flow for each vein and artery during each point of the cardiac cycle.

FIGS. 3a–b shows a phase contrast image of CSF pulsatile flow. The light area 46 in the center of FIG. 3a shows the outward flow of cranial spinal fluid during systole. The corresponding dark area of FIG. 3b shows the inward flow of CSF during diastole. The area 48 in the center of the CSF 46 depicts the spinal cord.

It has been found that in addition to blood and CSF flow, that spinal cord movement may also be considered in net flow considerations. However, it can be seen from a comparison of the flows of FIGS. 5a–c that ignoring spinal cord movement may not result in significant error.

Flow of the CSF and spinal cord may be determined as part of a two step process. First the spinal cord 48 is marked as described above and a spinal cord oscillatory flow is determined as discussed above. Since the cross-sectional area of the cord moves as a unit, one or two pixel values may be sufficient to determine velocity. Under a preferred embodiment all pixels within the cord area are integrated (summed) to obtain an average cord velocity.

Next, a flow in the annular area of the CSF between lines 46 and 48 may be determined. An outer periphery 46 (i.e., the dura) of the CSF is marked. The pixels of the spinal cord 48 is excluded from area and velocity determinations of the CSF. As above, the area of the annular area is determined and a CSF flow may be determined from an average velocity.

Since the flow is in an annular area, the measurement of velocity is somewhat more complicated. To insure an accurate average of velocity, flow across the annulus may be determined by integrating a velocity of each pixel around the annulus.

With a knowledge of flows into and out of the cranial space of a the subject, the value I(t) may be determined. From I(t), a value for ICP may be determined once a cranial pressure gradient (dP/dz) has been calculated.

To determine dP/dz, the area below the foramen magnum is again considered. For example, where CSF and spinal cord oscillatory flow are considered within a confined space (e.g., mid C2 region), the value for dP/dz can be calculated or determined with a high degree of accuracy, using convention pressure-flow equations.

A determination of dp/dZ has not been widely used in the past in arteries or veins because of the elastic periphery of such conduits. Within the C2 vertebra, the dura of the CSF is attached to the surrounding bone and provides a rigid tube which facilitates accurate measurements.

Under a preferred embodiment, dP/dz may be calculated for the CSF using the Navier-Stokes equation or Womersley Pressure-Flow Relation within the annular area containing the CSF. Such calculations may be accurately based upon assumptions including: no in-plane velocities, rigid walls of the space and minimum curvature along an axis of the conduit.

Within the annular area bounding the CSF, the space between the spinal cord and dura bounding the CSF may be relatively precisely determined. A velocity across that determined space may also be determined (or may also have been determined during flow measurements). The pressure gradient waveform may be calculated using the Navier-Stokes equation. The Navier-Stokes equation includes two terms inertial and viscous loss.

$$-\rho(\delta v/\delta t + v \cdot \nabla v) + \mu \nabla^2 v = \nabla p$$

The inertial component of the pressure gradient is approximated by the first order central difference template of the time series images and the shear component is derived by using a pair of second order central difference operators. The sum of the shear and inertia components in the region of interest which includes only the CSF pixels where added to derive mean pressure for each phase of the cardiac cycle.

When Womersley pressure flow relationships are used, the CSF flow and its time derivative are used to derive the pressure gradient waveforms.

$$\partial P/\partial z = I(\partial Q/\partial t) + RQ$$

Figure 6A:
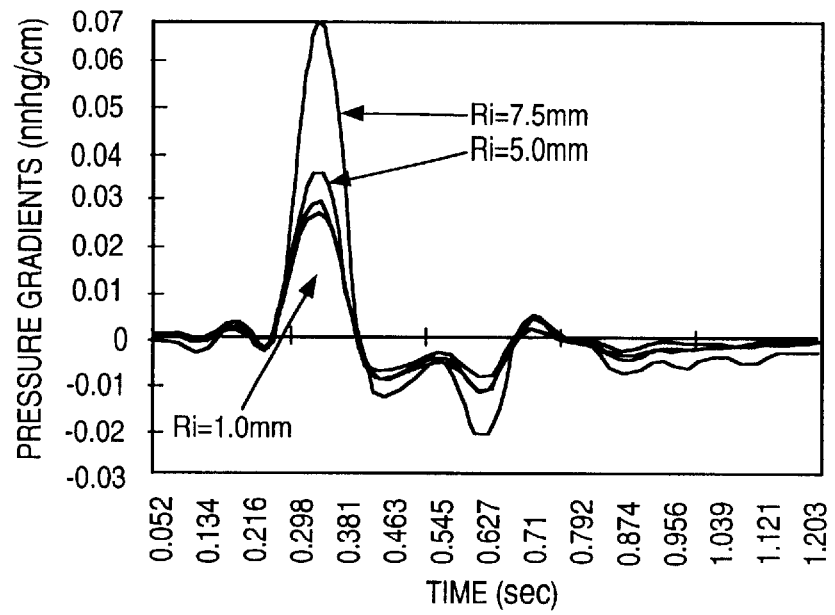
FIGS. 6a–b depicts pressure gradient calculations of the apparatus of FIG. 1.
Figure 6B:
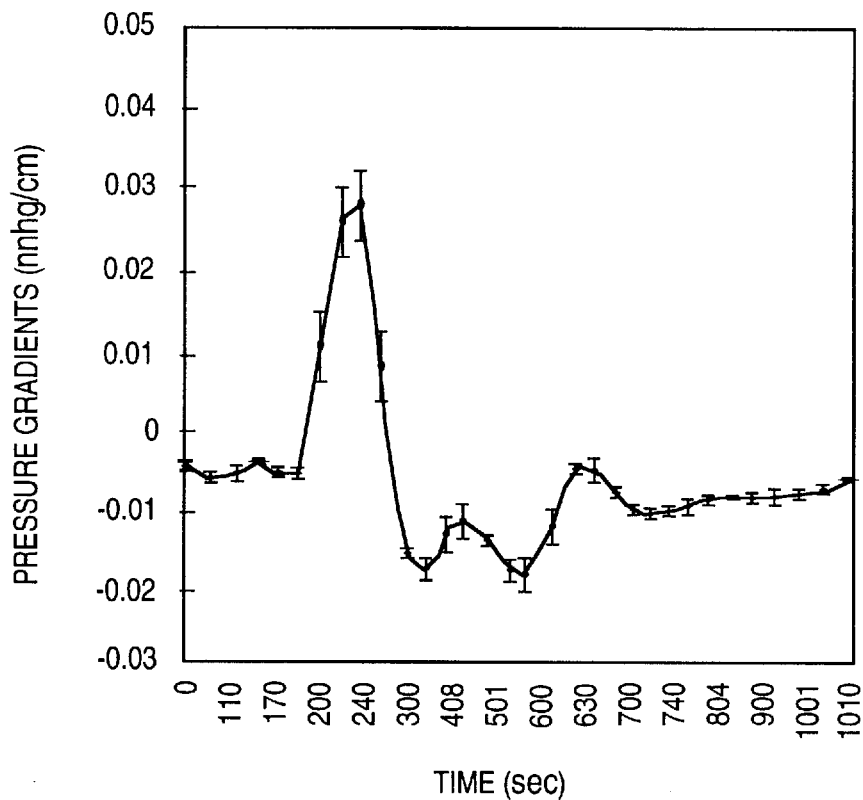

FIG. 6a provides a profile of pressure gradient versus time using the Womersley Pressure Flow Relationship. FIG. 6a shows pressure gradient waveforms derived from flow information for 4 different circular annulus cross-sectional areas. FIG. 6b is a gradient waveform derived using CSF velocity images and the Navier-Stokes equation.

As may be noted from FIG. 6a, the pressure gradient is highly dependent upon the size of the annulus. For example, the diameter of the CSF 46 for purposes of FIG. 6a was assumed to be 10.0 mm. To obtain a final value from the Womersley Pressure Flow Relationship the pressure gradient must be multiplied by an area of the annulus.

The concentric annulus model of FIG. 6a was used to evaluate the effect of the CSF cross-sectional area on the derived pressure gradient waveforms. Pressure gradient waveforms were derived for 4 models of concentric circular annulus with outer radius of 10 mm and inner radius that varied from 1 mm to 7.5 mm. The same CSF flow waveform was used for the 4 models. The derived waveforms are shown in FIG. 6a. The derived waveforms had similar shape but were different by a scale factor. This result suggests that normalization of the pressure gradients with the CSF cross-sectional area provides a way to obtain pressure gradients that are not velocity dependent, but are flow dependent. As a result, it is possible to compare pressure gradients derived form spinal canals that may differ in the CSF cross-sectional area.

FIG. 6b provides a pressure gradient derived from the velocity images and the Navier-Stokes equation.

Figure 9:
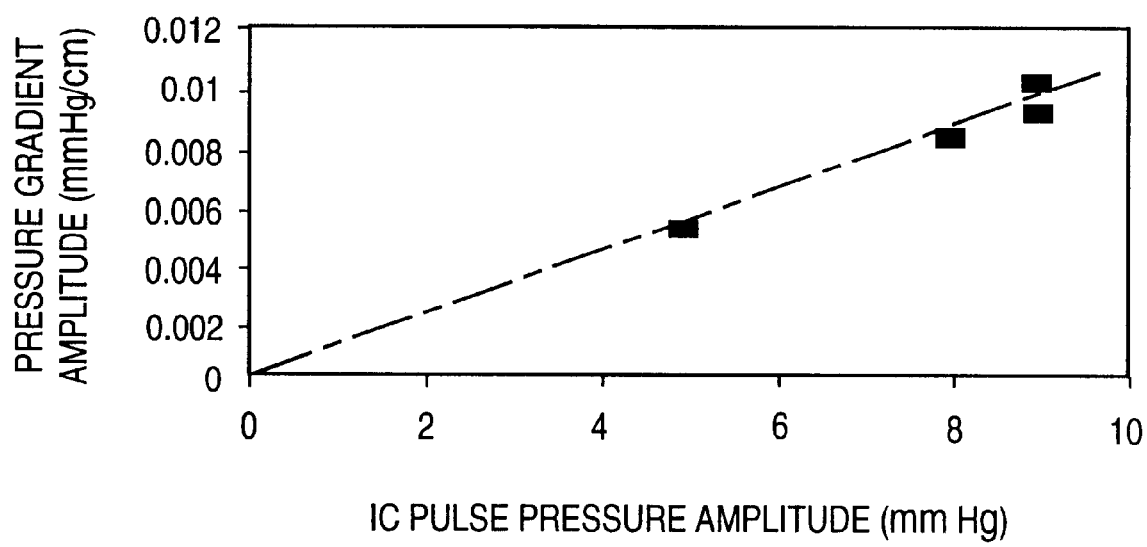
FIG. 9 depicts pressure gradient amplitude measured by the apparatus of FIG. 1.

FIG. 9 shows experimental results from a baboon comparing amplitude of MRI derived pulse pressure gradient and amplitude of invasively measured ICP pulse pressure at three different values of mean intracranial pressures. The relations obtained in this experiment are used when pulse pressure is estimated from MRI pressure gradients.

Figure 7:
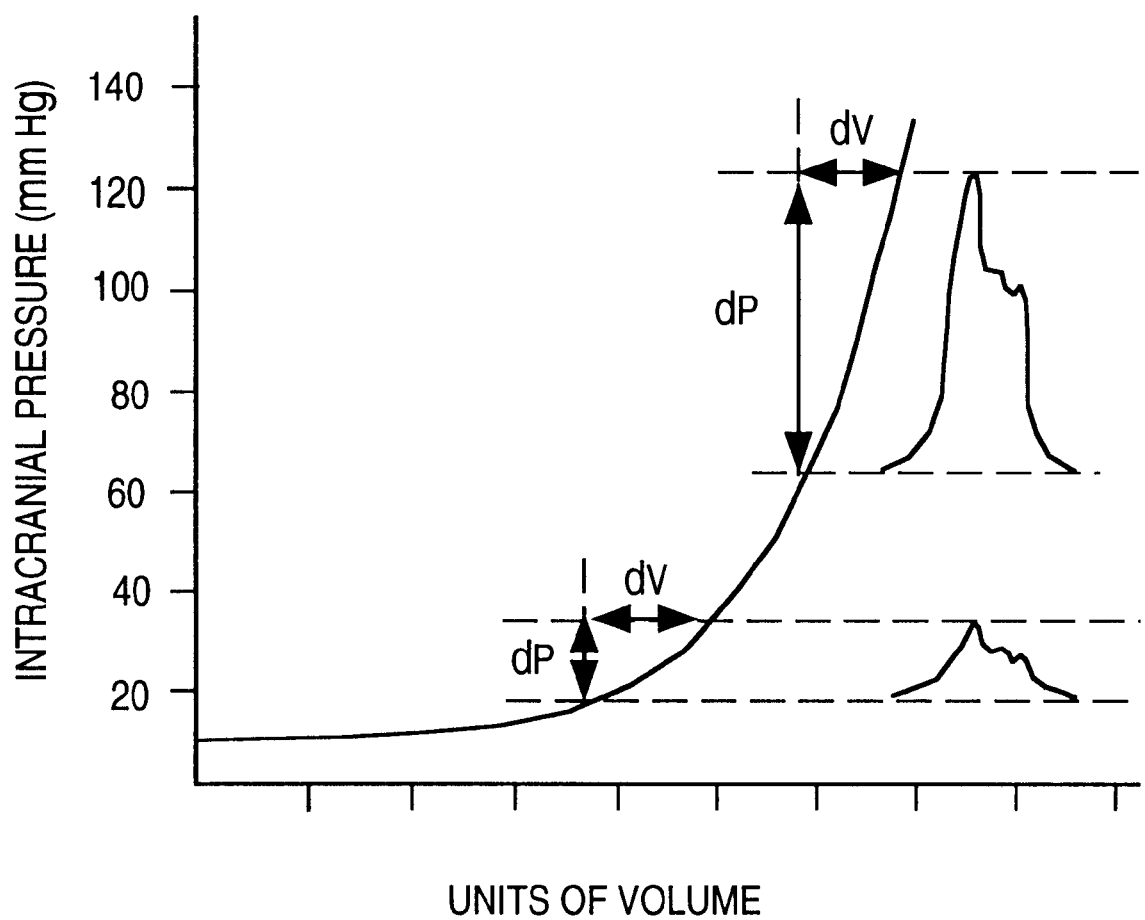
FIG. 7 depicts the elastance curve used by the apparatus of FIG. 1.
Figure 8:
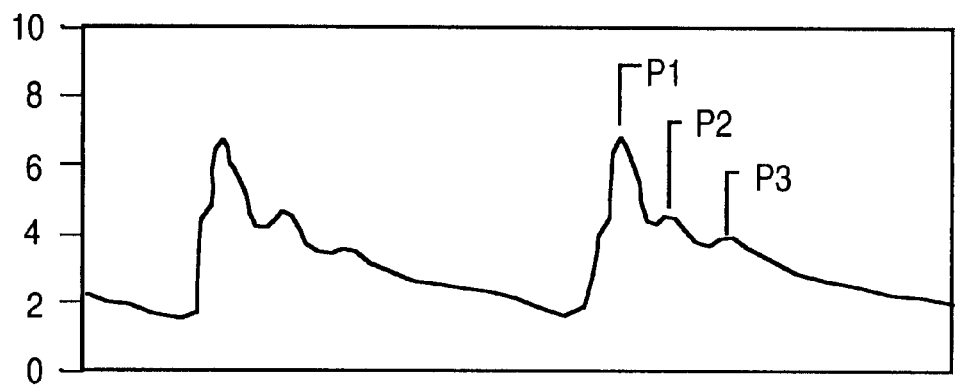
FIG. 8 depicts invasive recording of intracranial pressure forms causing the flows measured by the apparatus of FIG. 1.

FIG. 7 describes the ICP volume relationship which is described by the following expression:

$$P = P_1 \exp\{a(V - V_{eq})\} + P_o,$$

which is a monoexponential curve also known as the elastance curve. The derivative of this curve is therefore also an exponential curve therefore the following relationship exists between ICP and elastance:

$$dP/dV = a\{P - P_o\} = ac\{ICP\}.$$

DP/dV is estimated from the MRI derived pressure gradients and amplitude of the of the intracranial volume change. This value also referred to as elastance index is related to the ICP as expressed by the derivative of the elastance curve. The elastance curve is shown in FIG. 7. A relationship exists between the elastance index and intracranial pressure. (As is shown in FIG. 11).

FIG. 11 shows the relationship between the MRI derived elastance index and mean ICP. In specific, FIG. 10 shows the correlation between MRI derived elastance indexes and ICP for four patients (circles indicate data normalized for CSF area). As should be noted (neglecting the logarithmic scale) a linear relationship exists between elastance and ICP.

FIGS. 10a–b shows comparative data between pressure gradient and ICP. FIG. 11a shows a pressure gradient of a patient with a low ICP within a normal range. FIG. 11b shows a pressure gradient profile for a patient with an elevated ICP.

Table I shows comparative data from baboon experimentation. As shown, the MRI-derived data shows extremely good correlation to the invasively derived data.

TABLE I

| | | Invasive | | | MRI-Derived | |
|---|---|---|---|---|---|---|
| | HR (bpm) | Mean ICP (mmHg) | HR (MRI) (bpm) | PTP Pr Grd mm/Hg/cm) | PTP Vol. Change | Elastance dP/dV |
| Rest | 80 | 12 | 80 | 0.029 | 0.17 | 0.16 |
| High | 82 | 24 | 81 | 0.023 | 0.09 | 0.26 |
| Low | 84 | 9 | 86 | 0.016 | 0.17 | 0.093 |

Table II shows comparative data for four patents. As with the baboon data, the MRI derived data shows extremely good correlation with the invasively derived data.

TABLE II

| | HR (ICU) (bpm) | Mean ICP (mmHg) | PTP ICP (mmHg) | HR (MRI) (bpm) | PTP Pr Grad (mm/Hg/cm) (A) | CSF flow area (cm$^2$) (C) | PTP Vol Chng (cc) (B) | Elast. dP/dV = (A/B) | Elast. Norm. for CSF ar (A/B) × C |
|---|---|---|---|---|---|---|---|---|---|
| Pt. #1 | 69 | 10 | 3.75 | 81 | 0.016 | 2.43 | 0.44 | 0.036 | 0.087 |
| Pt. #2 | 100 | 8 | 3.0 | 94 | 0.018 | 1.36 | 0.36 | 0.049 | 0.067 |
| Pt. #3 | 110 | 16 | 6.75 | 75 | 0.098 | 2.91 | 1.38 | 0.071 | 0.207 |
| Pt. #4* | — | 24 | — | 82 | 0.062 | 0.60 | 0.073 | 0.845 | 0.547 |

\* = invasive ICP measured with lumbar puncture.

A preliminary comparison of invasive pressure measurements and MRI-derived measurements were obtained from two baboon studies (the second study is shown in Table I) and from four patients who were monitored for ICP at the time of the MRI study (Table II). A summary of the results and their importance to this project are described below.

In the first experiment, mean ICP was controlled by changing the fluid volume in the CNS (i.e., the transcranial blood flow was unchanged). Under these conditions, a linear relationship may be found between the peak to peak (PTP) amplitude of the MRI-derived CSF pulsatile pressure gradient and the PTP amplitude of the ICP. The results are shown in FIG. 9. A similar correlation was found between the PTP amplitude of the MRI-derived pressure gradients and the means ICP.

The experiment was repeated. This time the mean ICP was modified by restricting the jugular venous outflow (Valsalva maneuver). In this experiment, the hemodynamic state is different at each level of the mean ICP. As expected, there was no correlation between the PTP amplitude of the MRI-derived pressure gradients and the mean ICP. However, it would be expected to find a correlation between MRI-derived elastance (dV/dP) and means ICP.

The elastance index can be estimated from the ratio of the PTP amplitude of the MRI-derived pressure gradients and the PTP amplitude of intracranial volume change. The results of the second experiment are summarized in Table I. As expected, when hemodynamic changes occurs in conjunction with change in the mean ICP, the elastance, and not the PTP pressure gradients, is correlated with the mean ICP value.

Pressure measurements were also obtained from four patients who underwent an MRI study (Table II) and were monitored for ICP with a short external ventricular drainage catheter (EVD) which was inserted into their lateral ventricle. The measured and derived parameters from the patients are summarized in Table II.

Patient 1 and 2 had mean ICP values within the normal range, while patient 3 had an elevated mean ICP, and patient 4 had extremely elevated ICP. The ICP measurements covers a large portion of the practical range expected for ICP measurements. Though the MRI measurements and the ICP recordings were not measured simultaneously (measurements were made from an hour to several hours apart), there was good correspondence between mean ICP, measured invasively, and the MRI-derived estimate for the elastance. It is clear that using the CSF flow area for normalization of the PTP pressure gradients improves the correspondence between the elastance and the mean ICP. Actual ICP recordings and the corresponding MRI-derived pressure gradients are shown in FIGS. 11a and 11b, respectively. These results indicate that the sensitivity of the MRI measurements are within the range needed to differentiate between normal and elevated ICP.

Under another illustrated embodiment of the invention, an automated method (Time Series Method) is provided for segmentation of flow areas (i.e., fluid conduits) in blood vessels, CSF spaces, or any region that exhibits a specific dynamic behavior that is different from the surrounding region. (e.g. pulsatile blood flow versus static tissue). This technique automates the calculation of blood and CSF flow rates, which are intermediate steps in the method for non-invasive measurements of intracranial pressure (ICP). However, it can be used in any application that requires identification of the lumen region of vessels that contains non-steady flow. Such applications include the calculation of blood flow in any area in the body, as well as CSF flow rates.

One of the significant aspects of the embodiment is the use of dynamic information in time-series images to identify and segment the lumen. Prior techniques have used the spatial information in a single image for this purpose. The prior techniques have been limited by the contrast to noise of the single image used for determination of the border of the lumen (e.g. blood vessel). The new technique utilizes multiple images for identification of the lumen region and therefore it utilizes information with an inherently higher contrast to noise ratio.

A second unique feature of this new technique is a built-in mechanism to identify an optimal threshold criterion for identification of the lumen region. Unlike many previous techniques, which use arbitrary threshold values to differentiate between the lumen region and the surrounding background, an optimal threshold is identified based on the information contained in the images. An additional advantage of this new technique is the possibility to segment several vessels' lumen simultaneously when the flow dynamics in these vessels is similar.

It has been found that volumetric flow rates waveforms can be calculated from multiple time series images that depict velocities across the lumen as a function of time. The flow rate at each time point is then calculated by summation of the velocity values in all image elements (pixels) that are included in the flow area region (i.e., the lumen). Therefore, identification of the lumen region is required for volumetric flow calculation. Most commonly used imaging modalities to obtain flow rates in medical applications are the Doppler ultrasound technique and the MRI dynamic phase contrast techniques. The new method is based upon images that are obtained with MRI.

For example, dynamic MRI phase contrast technique can provide a set of 32 images (each providing a velocity map) which together represents the flow dynamics during one cardiac cycle. The new method may be applied to segment flow area regions for automated calculation of blood flow in all major blood vessel that supply blood to and from the brain and for automated calculation of CSF flow between the cranium and the spinal canal.

In general, the new method may include five basic steps. As a first step a reference location may be selected (e.g., by clicking on a pixel or group of pixels) inside the flow area (within the lumen of the vessel). Next a time-varying velocity waveform is determined at the selected pixel location, which we refer to as the "reference waveform". A map is prepared of the cross-correlation values for the velocity waveforms at all pixel location in the image (or a region of interest within it) between the time varying velocity waveforms and the reference waveform. The optimal threshold value range to be used for identification of the lumen region may then be determined. Finally the boundary of the regions with cross-correlation values above the threshold may be determined.

Figure 12A:
FIG. 12A depicts one image of a sequence of 32 velocity-encoded images generated by the system of FIG. 1 showing a selected pixel inside a vessel lumen.

The steps may now be discussed in detail. To begin the process, a reference pixel location may be selected within the vessel. An example is shown in FIG. 12a. One of the 32 images of the velocity encoded MRI images obtained through an axial plane in the neck is shown. The 32 images may represent a time-sequence of one cardiac cycle. The cross-mark indicates the pixel location selected as a reference.

Figure 12B:
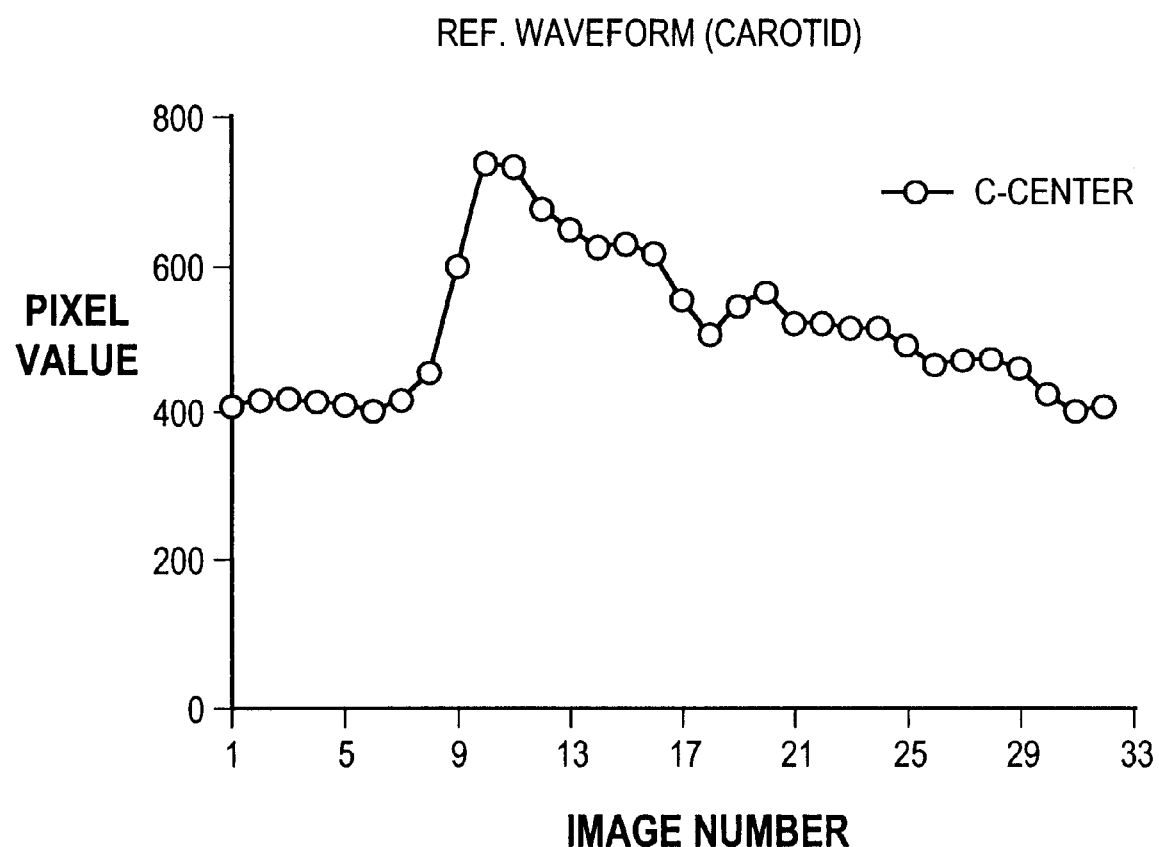
FIG. 12B depicts a velocity versus time waveform from the location of the selected pixel of FIG. 12A.

A time varying velocity waveform (i.e., "the reference waveform") may be generated for the selected pixel location using the velocity data of the selected pixel from the 32 images. An example of a reference waveform is shown in FIG. 12b. This waveform is obtained by plotting the pixel velocity value, which in our case is proportional to the fluid velocity, at the same selected pixel location from all 32 images. This waveform describes the velocities as a function of time at this location during a cardiac cycle.

A time varying velocity waveform may also be prepared for every other pixel in the images. A cross-correlation among the velocity waveforms may be prepared next. For each pixel location in the selected region of interest the cross correlation (CC) value between the reference waveform and the time varying waveform at that other pixel location is calculated. The possible CC values range from 1 to −1. High CC values indicates high similarity between the current and reference waveform. The maximum value of one indicates identity between the current waveform and the reference waveform. Lower values indicate decreased in similarity.

Figure 13:
FIG. 13 depicts a cross-correlation map of the image of FIG. 12.

The CC value is calculated using the following expression, which is well-known in the literature to those of skill in the art:

$$P_{XY} = \frac{\sum_{k=0}^{N}(R_k - \overline{R})(XY_k - \overline{XY})}{\sqrt{\sum_{k=1}^{N}(R_k - \overline{R})^2 \sum_{k=1}^{N}(XY_k - \overline{XY})^2}} \quad (1)$$

where $P_{xy}$ is the cross correlation value at pixel location XY, R is the reference waveform, k is the time index of the time-series image and N is the total number of images in the time series. A cross correlation map that was obtained for the image region of FIG. 12 that includes the blood vessels is shown in FIG. 13. Higher image intensity (i.e., a lighter color in FIG. 13) indicates higher CC value.

An optimal threshold value may be determined next. It is evident that the velocity waveforms at different image location within the lumen are of similar dynamic behavior. Therefor these waveforms are highly correlated and would have a relatively high CC value. The following step is used to determine the CC value that will be used for differentiation between pixels inside the lumen and outside (i.e., in the surrounding region). Pixels with CC value above the threshold will be segmented as pixels that are included in the segmented lumen region.

Figure 14:
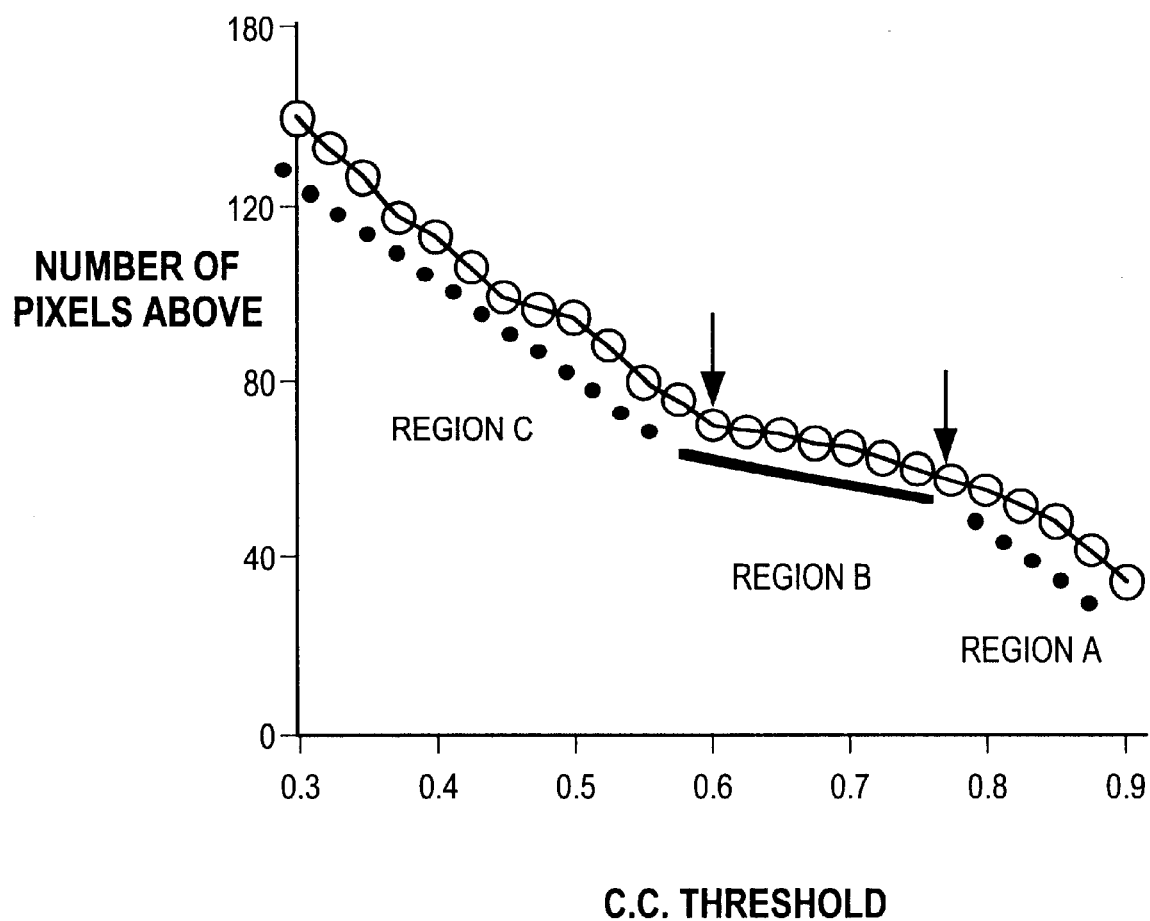
FIG. 14 is a histogram generated by the system of FIG. 1 relating CC threshold values with the number of pixels having values above the threshold and wherein the histogram shows a first and third areas A and C where the number of pixels is highly dependent upon the threshold chosen and a second area B with a relatively flat slope indicating an optimal threshold area.

The processor 18 may be used for the automatic selection of the optimal CC threshold value. The number of pixels with CC value above a certain CC threshold is calculated for threshold values between 0.3 to 0.9 at 0.025 intervals. An example of such graph obtained from an image containing the blood vessel region is shown in FIG. 14. This plot has three distinct regions. Two regions A, C in which the number of pixels decreases rapidly with increase in threshold value and a region B in between where the number of pixel detected are relative constant and do not change much with increases in the threshold value.

In the first two regions A, C the CC value is either too low, pixels from the background region are detected with decrease in CC value, or too high, where only part of the pixels inside the vessel lumen are detected. The flat region B indicates the intermediate region where most or all the pixels inside the lumen are detected and none or very few pixels are detected outside the lumen region. Therefore a threshold value in the "flat" region of the graph is optimal for identification of the lumen region. The "flat" region is identified by search for region with the highest derivative values. The threshold may be selected as an average value for that region B or offset by some value, depending upon the shape of this "flat" region.

Edge detection of the lumen's contour may be considered next. In the final step, a simple edge tracking method may be used to find the contour of the lumen region. Often a few isolated pixels in the surrounding regions have CC values above the threshold due to noise present in the data. The edge-tracking step excludes these pixels from the cluster of connected (locus of) pixels that constitute the outline of the lumen.

Figure 15:
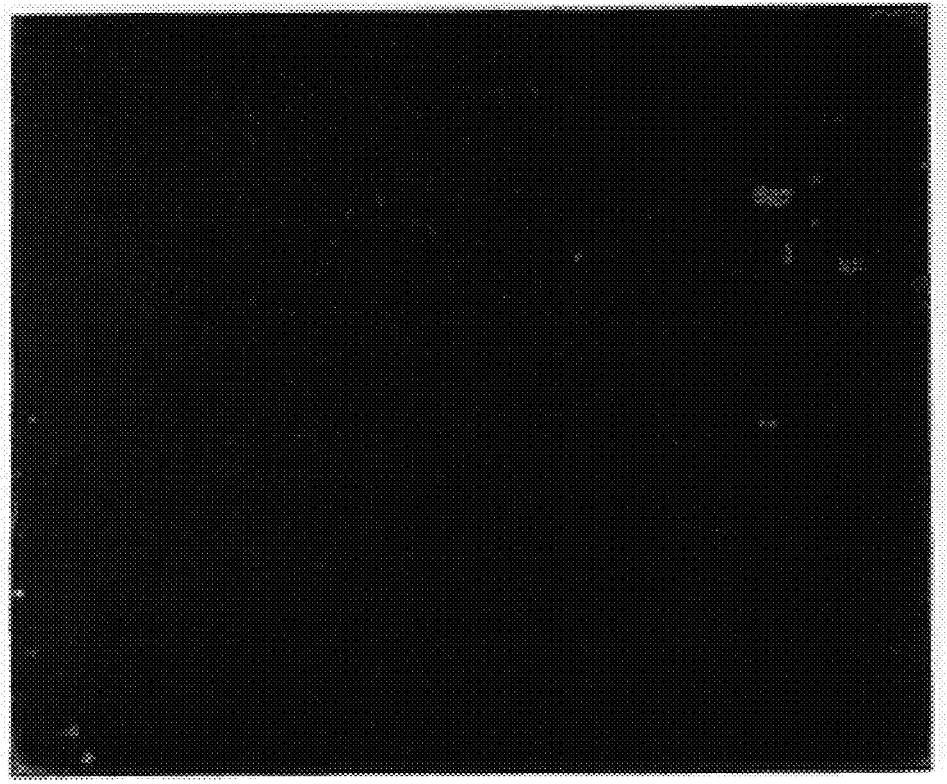
FIG. 15 depicts picture elements identified by the system of FIG. 1 with values above the selected threshold shown in white, thereby identifying the vessel lumen.
Figure 16A:
FIG. 16A depicts one image of a sequence of 32 CSF velocity-encoded images that may be generated by the system of FIG. 1 with the location of a reference picture element "x" inside the CSF lumen.
Figure 17:
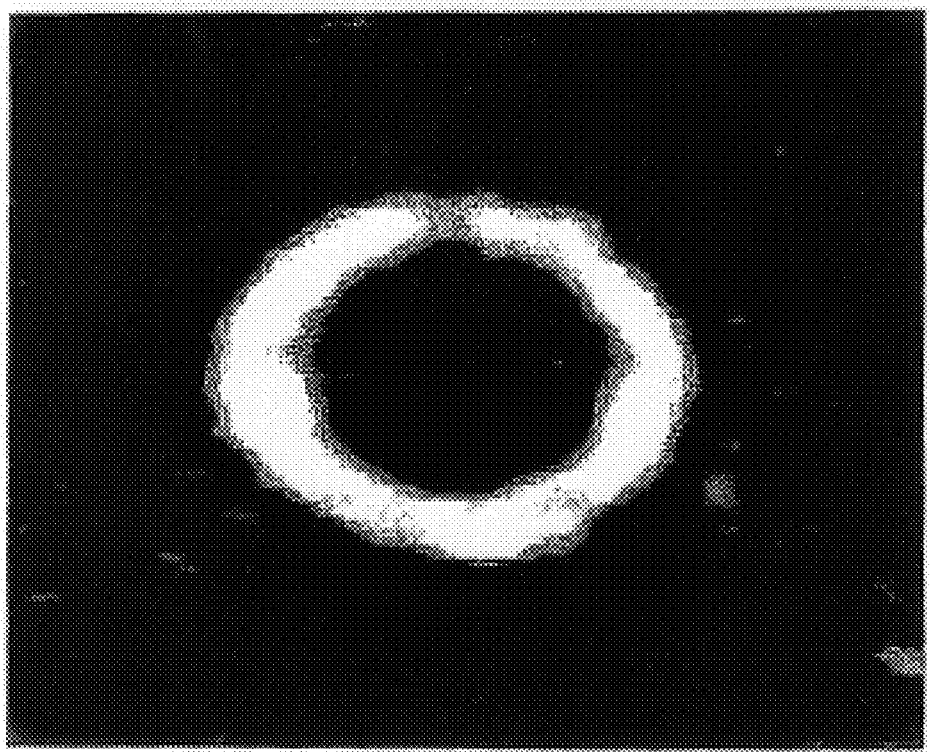
FIG. 17 shows a CC map obtained by the system of FIG. 1 from the time-series sequence of FIG. 16.
Figure 18:
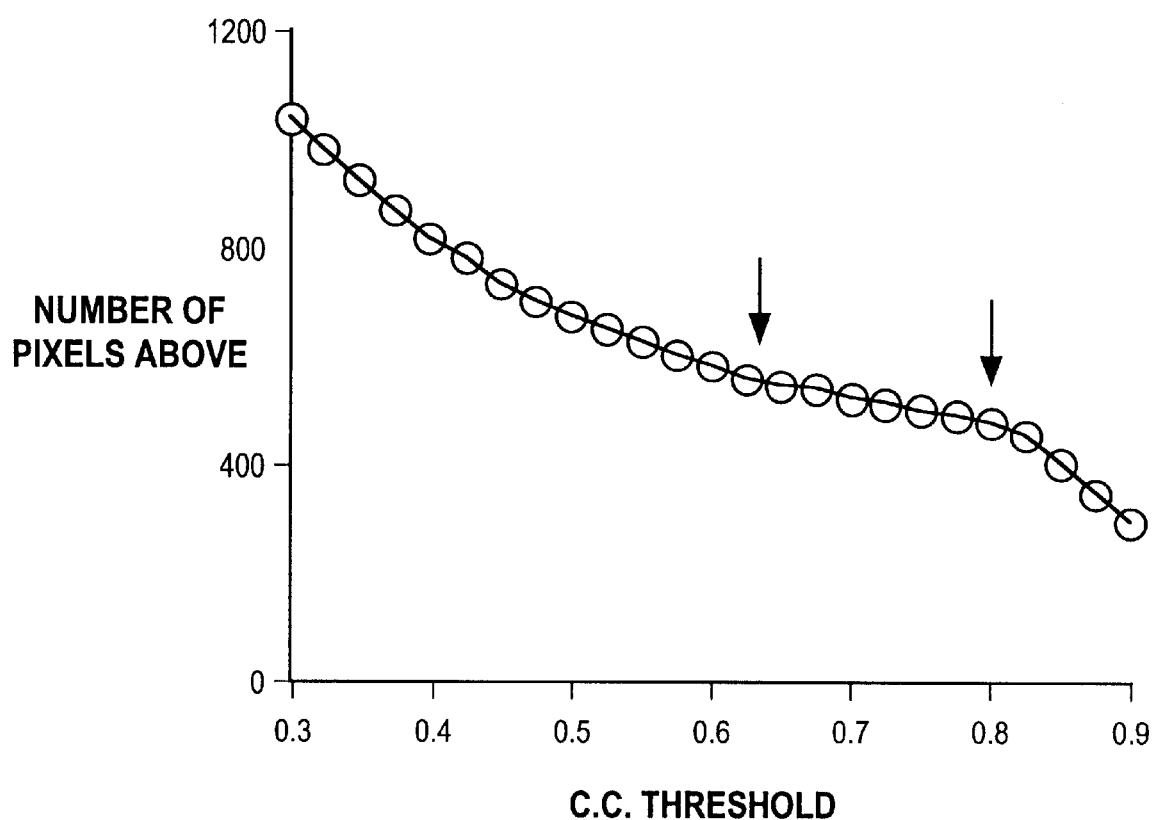
FIG. 18 is a histogram similar to the one of FIG. 14 generated by the system of FIG. 1 relating CC threshold values with the relative number of picture elements having values above the threshold and wherein the histogram shows a first and third areas where the number of pixels is highly dependent upon the threshold chosen and a second area with a flat slope (identified by the two arrows) indicating an optimal threshold area.
Figure 19:
FIG. 19 shows a CSF lumen identified by the automated technique of the system of FIG. 1 in which two boundary lines were automatically identified, where the area inside the inner boundary line (cord) was subtracted from the area inside the outer boundary line to obtain the CSF lumen and where, in many cases the CSF is not a closed circular shape and might differ depending on the patient, but where the automated method of the system of FIG. 1 can detect any shape of vessel, even if the shapes of the boundary lines are fragmented.

There are many techniques to identify the contour of a segmented region. The selected method uses a binary edge detection algorithm to obtain efficient edge detection. Using the edge detection algorithm, the CC map is converted to a binary image where pixels with CC value equal to or above the threshold are assigned the value of one. Pixels with CC value below the threshold are assigned the value zero. The lumen contour is identified by searching for the nearest neighbor pixels with a value of one that are connected and are bordering with pixels with a value of zero. An example of a vessel lumen with the contour identified automatically using this technique is shown in FIG. 15.

The relative performance of the new technique may be considered next. The time-series technique was evaluated for reproducibility and was compared with manual segmentation. Fifteen sets of data were tested by 5 observers with different skill levels. Each set contains two image-series, one series used to image blood flow in 6 blood vessels and the second to image cerebrospinal fluid (CSF) flow. The table below demonstrates the improvement in the reproducibility of lumen segmentation with this technique. The reproducibility was determined by comparing the mean standard deviation of the number of pixels identified as the lumen region using manual tracing and the automated time-series method.

TABLE 1

Comparison between reproducibility of manual
and automated segmentation

| VESSELS | | | MANUAL TECH. Mean St. dev. | AUTOMATED TECH. Mean St. dev. |
|---|---|---|---|---|
| Carotid Artery | Areas | R | 9.9 | 2.0 |
| | | L | 9.6 | 2.4 |
| | M. Flow | | 30.6 | 5.6 |
| Jugular Vein | Areas | R | 18.5 | 4.0 |
| | | L | 7.8 | 4.2 |
| | M. Flow | | 56.7 | 12.3 |
| Vertebral Artery | Areas | R | 9.2 | 1.8 |
| | | L | 8.3 | 2.0 |
| | M. Flow | | 23.4 | 5.7 |
| CSF | Area | | 30.3 | 7.4 |
| | Osc. Flow | | 1.3 | 0.6 |

The mean standard deviation of pixel number (area),and mean total flow (mL/min), are listed in the table above. The mean standard deviations of the automated method are significantly smaller than the manual method. For all vessel types, the reproducibility is improved by a factor of approximately four.

The accuracy of the technique was estimated by comparing the lumen area found by the manual tracking with the one found using the automated technique. The results are summarized in table 2. The % change of pixel number, and change in mean flow from manual method to the automated method of each vessel are listed.

TABLE 2

The relative changes in average lumen sizes
and in total mean flows obtained by the two techniques.

| VESSELS | | | % CHANGE OF LUMEN AREA AND MEAN FLOW FROM MANUAL TO AUTO. |
|---|---|---|---|
| Carotid Artery | Areas | R | 34.9 |
| | | L | 38.7 |
| | Flow (ml/min) | | 12.4 |
| Jugular Vein | Areas | R | 15.1 |
| | | L | 46.8 |
| | Flow (ml/min) | | 15.3 |
| Vertebral Artery | Areas | R | 67.3 |
| | | L | 61.7 |
| | Flow (ml/min) | | 23.8 |
| CSF | Area | | 22.6 |
| | Osc. Flow | | 8.1 |

On the average, the area identified by the automated technique was larger. Since there are no available means to accurately measure the true lumen size, we hypothesize that the automated technique is more accurate because it is known that manual segmentation usually tends to underestimate the true vessel lumen. When MRI phase contrast images are used for segmentation of the lumen, manual segmentation is effected by the setting of the image contrast and by the selected image that is used as a reference. The vessel lumen appears largest only on the images acquired during peak systolic flow. Furthermore, the low contrast of the slow flowing fluid near the vessel wall may often be misjudged as part of the surrounding static tissue.

The detected pixel numbers are higher with the automated method. Since users choose the image with highest contrast, which means that the flow velocity is maximum and the cross-sectional area of the lumen is not necessarily largest, the manual method produces smaller region of interest than the automated method. (With naked human eyes, it is difficult to detect slow flowing pixels at the edge of the vessel. (Also, the resolution of the computer monitor affects the user's decision.) The % change is higher with smaller vessels, such as vertebral arteries and the left jugular vein, since one pixel width represent a larger % change in the lumen area. In general, lumen sizes obtained by a skilled observer had the smallest area difference between the automated and the manual techniques. An example is shown in FIG. 21. Both the automated contours (red) and the manually traced contours (brown) are shown for the carotid and vertebral artery, the jugular vein, and the CSF flow area.

To demonstrate that the technique works for segmentation of lumens other than blood vessel we applied the technique to segment and contour the CSF flow area in the cervical spine. FIGS. 16–19 demonstrate the technique for MRI images obtained to quantify CSF flow. These figures correspond to FIGS. 11–15 and 21 that were obtained for MRI images obtained to quantify flow in blood vessels.

Figure 20:
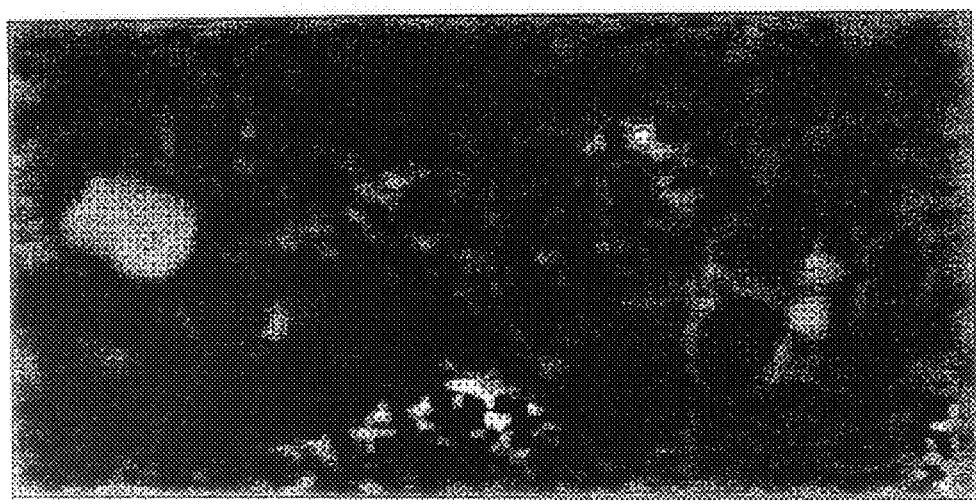
FIG. 20 shows a number of lumens identified by selection of a single point within a single lumen by the system of FIG. 1.
Figure 21A:
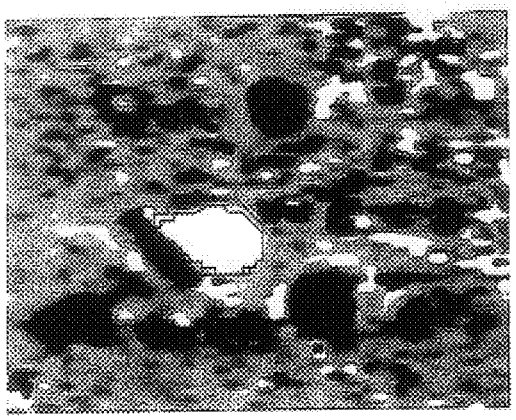
FIG. 21 shows contours of blood vessels identified manually by a skilled observer and by the automated method of the system of FIG. 1 for several types of blood vessels and for a CSF lumen and where the performance of the automated model is similar to that of the skilled observer.
Figure 21B:
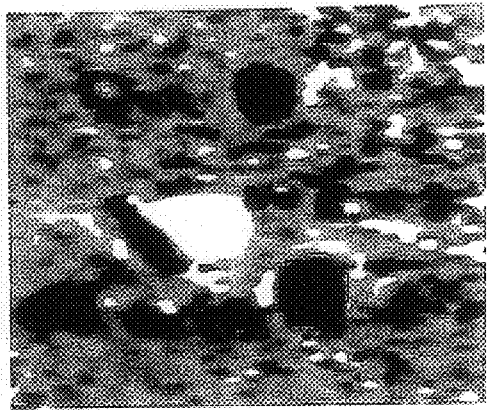
Figure 21C:
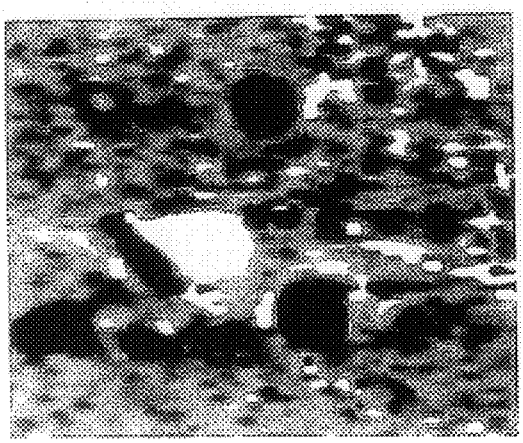
Figure 21D:
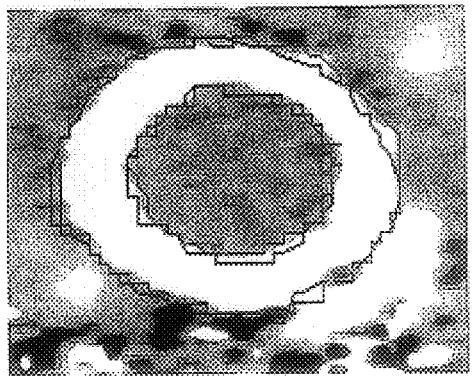

FIG. 20 demonstrates that the method can be used to segment multiple vessels using only one reference waveform.

A specific embodiment of a novel method and apparatus for determining intracranial pressure according to the present invention has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention any and all modifications, variations, or equivalents that fall within the true spirit and scope of the basic underlying principles disclosed and claimed herein.

What is claimed is:

1. A method for identifying a fluid conduit of a human body within a set of images collected over a portion of a cardiac cycle and where each image of the set of images is formed by a plurality of image elements, such method comprising the steps of:

selecting a reference image element within the fluid conduit from the plurality of image elements;

determining a velocity profile of each of the image elements over the cardiac cycle; and identifying the fluid conduit by correlating the velocity profile of the reference element with velocity profiles of at least some of the other image elements.

2. A method for identifying a fluid conduit of a human body within a set of images collected over a portion of a cardiac cycle and where each image of the set of images is formed by a plurality of image elements, such method comprising the steps of:

collecting 32 images over the cardiac cycle as the set of images;

selecting a reference image element within the fluid conduit from the plurality of image elements;

determining a velocity profile of each of the image elements over the cardiac cycle; and identifying the fluid conduit by correlating the velocity profile of the reference element with velocity profiles of at least some of the other image elements.

3. A method for locating the fluid conduit of a human body within a set of images collected over a portion of a cardiac cycle and where each image of the set of images is formed by a plurality of image elements, such method comprising the steps of:
- selecting a reference image element within the fluid conduit from the plurality of image elements using pixels as image elements;
- determining a velocity profile of each of the image elements over the cardiac cycle; and
- identifying the fluid conduit by correlating the velocity profile of the reference element with velocity profiles of at least some of the other image elements.

4. The method for identifying the fluid conduit as in claim 3 further comprising calculating a cross-correlation value for each pixel.

5. The method for identifying the fluid conduit as in claim 4 further comprising solving for the cross-correlation value by evaluating the equation $$P_{XY} = \frac{\sum_{k=0}^{N}(R_k - \overline{R})(XY - \overline{XY})}{\sqrt{\sum_{k=1}^{N}(R - \overline{R})^2 \sum_{k=1}^{N}(XY - \overline{XY})^2}},$$

where $P_{XY}$ is the cross-correlation value at pixel location XY, R is the reference waveform, k is a time index of the cardiac cycle and N is a total number of images in the cardiac cycle.

6. The method for identifying the fluid conduit as in claim 4 further comprising selecting a correlation threshold between the cross-correlation value of the reference pixel and the other pixels.

7. The method for identifying the fluid conduit as in claim 6 further comprising selecting the correlation threshold from a region of a relatively constant number of pixels that have values above a selected threshold value.

8. The method for identifying the fluid conduit as in claim 7 further comprising forming an outline of the fluid conduit based upon the correlated velocity profiles.

9. The method for identifying the fluid conduit as in claim 8 wherein the step of finding the fluid conduit further comprises identifying a group of adjacent pixels of the pixels with correlated velocity profiles.

10. The method for identifying the fluid conduit as in claim 9 further comprising identifying a locus of points surrounding the grouped pixels.

11. Apparatus for identifying a fluid conduit of a human body within a set of images collected over a portion of a cardiac cycle and where each image of the set of images is formed by a plurality of image elements, such apparatus comprising:
- means for selecting a reference image element within the fluid conduit from the plurality of image elements;
- means for determining a velocity profile of each of the image elements over the cardiac cycle; and
- means for identifying the fluid conduit by correlating the velocity profile of the reference element with velocity profiles of at least some of the other image elements.

12. Apparatus for identifying a fluid conduit of a human body within a set of images collected over a portion of a cardiac cycle and where each image of the set of images is formed by a plurality of image elements, such apparatus comprising:
- means for collecting 32 images over the cardiac cycle as the set of images;
- means for selecting a reference image element within the fluid conduit from the plurality of image elements;
- means for determining a velocity profile of each of the image elements over the cardiac cycle; and
- means for identifying the fluid conduit by correlating the velocity profile of the reference element with velocity profiles of at least some of the other image elements.

13. Apparatus for identifying a fluid conduit of a human body within a set of images collected over a portion of a cardiac cycle and where each image of the set of images is formed by a plurality of image elements, such apparatus comprising:
- means for selecting a reference image element within the fluid conduit from the plurality of image elements using pixels as image elements;
- means for determining a velocity profile of each of the image elements over the cardiac cycle; and
- means for identifying the fluid conduit by correlating the velocity profile of the reference element with velocity profiles of at least some of the other image elements.

14. The apparatus for identifying the fluid conduit as in claim 13 further comprising means for calculating a cross-correlation value for each pixel.

15. The apparatus for locating the fluid conduit as in claim 14 further comprising means for solving for the cross-correlation value by evaluating the equation $$P_{XY} = \frac{\sum_{k=0}^{N}(R_k - \overline{R})(XY - \overline{XY})}{\sqrt{\sum_{k=1}^{N}(R - \overline{R})^2 \sum_{k=1}^{N}(XY - \overline{XY})^2}},$$

where $P_{XY}$ is the cross-correlation value at pixel location XY, R is the reference waveform, k is a time index of the cardiac cycle and N is a total number of images in the cardiac cycle.

16. The apparatus for locating the fluid conduit as in claim 14 further comprising means for selecting a correlation threshold between the cross-correlation value of the reference pixel and the other pixels.

17. The apparatus for identifying the fluid conduit as in claim 16 further comprising means for selecting the correlation threshold from a region of a relatively constant number of pixels that have values above a selected threshold value.

18. The apparatus for identifying the fluid conduit as in claim 17 further comprising means for forming an outline of the fluid conduit based upon the correlated velocity profiles.

19. The apparatus for identifying the fluid conduit as in claim 18 wherein the means for finding the fluid conduit further comprises means for identifying a group of adjacent pixels of the pixels with correlated velocity profiles.

20. The apparatus for identifying the fluid conduit as in claim 19 further comprising means for identifying a locus of points surrounding the grouped pixels.

21. Apparatus for identifying a fluid conduit of a human body within a set of images collected over a portion of a cardiac cycle and where each image of the set of images is formed by a plurality of image elements, such apparatus comprising:
- a pointer adapted to select a reference image element within the fluid conduit from the plurality of image elements;
- an velocity processor adapted to determine a velocity profile of each of the image elements over the cardiac cycle; and a correlation processor adapted to identify the fluid conduit by correlating the velocity profile of the reference element with velocity profiles of at least some of the other image elements.

22. The apparatus for identifying the fluid conduit as in claim 21 further comprising an image compiler adapted to collect 32 images over the cardiac cycle.

23. The apparatus for identifying the fluid conduit as in claim 21 further comprising a pixel processor adapted to use pixels as image elements.

24. The apparatus for identifying the fluid conduit as in claim 23 further comprising a cross-correlation processor adapted to calculate a cross-correlation value for each pixel.

25. The apparatus for identifying the fluid conduit as in claim 24 wherein the cross-correlation processor further comprising an arithmetic unit adapted to solve for the cross-correlation value by evaluating the equation $$P_{XY} = \frac{\sum_{k=0}^{N}(R_k - \overline{R})(XY - \overline{XY})}{\sqrt{\sum_{k=1}^{N}(R - \overline{R})^2 \sum_{k=1}^{N}(XY - \overline{XY})^2}},$$

where $P_{XY}$ is the cross-correlation value at pixel location XY, R is the reference waveform, k is a time index of the cardiac cycle and N is a total number of images in the cardiac cycle.

26. The apparatus for identifying the fluid conduit as in claim 24 further comprising a threshold processor adapted to select a correlation threshold between the cross-correlation value of the reference pixel and the other pixels.

27. The apparatus for identifying the fluid conduit as in claim 26 further comprising a derivative processor adapted to select the correlation threshold from a region of a relatively constant number of pixels that have values above a selected threshold value.

28. The apparatus for identifying the fluid conduit as in claim 27 further comprising an outline processor adapted to form an outline of the fluid conduit based upon the correlated velocity profiles.

29. The apparatus for identifying the fluid conduit as in claim 28 wherein the outline processor finding the fluid conduit further comprises a comparison processor adapted to identify a group of adjacent pixels of the pixels with correlated velocity profiles.

30. The apparatus for identifying the fluid conduit as in claim 29 further comprising a locus processor adapted to identify a locus of points surrounding the grouped pixels.

31. A method for segmentation of a region that exhibits a specific dynamic behavior that is different from a surrounding region and for determination of a boundary of a spinal cord from a set of images collected over a portion of a cardiac cycle and where each image of the set of images is formed by a plurality of image elements, such method comprising the steps of:

selecting a reference image element within the spinal cord from the plurality of image elements;

determining a velocity profile of each of the image elements over the cardiac cycle; and identifying the image elements that comprise the spinal cord by correlating the velocity profile of the reference element with velocity profiles of the other image elements.

32. The method for segmentation as in claim 31 further comprising determining an optimal cross correlation threshold based upon a relative number of pixels that have values above a threshold value as a function of that threshold value.

33. An apparatus for segmentation of a region that exhibits a specific dynamic behavior that is different from a surrounding region and for determination of a boundary of a spinal cord from a set of images collected over a portion of a cardiac cycle and where each image of the set of images is formed by a plurality of image elements, such apparatus comprising:

means for selecting a reference image element within the spinal cord from the plurality of image elements;

means for determining a velocity profile of each of the image elements over the cardiac cycle; and means for identifying the image elements that comprise the spinal cord by correlating the velocity profile of the reference element with velocity profiles of the other image elements.

34. The apparatus for segmentation as in claim 33 further comprising means for determining an optimal cross correlation threshold based upon a relative number of pixels that have values above a threshold value as a function of that threshold value.

35. An apparatus for segmentation of a region that exhibits a specific dynamic behavior that is different from a surrounding region and for determination of a boundary of a spinal cord from a set of images collected over a portion of a cardiac cycle and where each image of the set of images is formed by a plurality of image elements, such apparatus comprising:

a pointer adapted to select a reference image element within the spinal cord from the plurality of image elements;

a velocity processor adapted to determine a velocity profile of each of the image elements over the cardiac cycle; and a correlation processor adapted to identify the image elements that comprise the spinal cord by correlating the velocity profile of the reference element with velocity profiles of the other image elements.

36. The apparatus for segmentation as in claim 35 further comprising a derivative processor adapted to determine an optimal cross correlation threshold based upon a relative number of pixels that have values above a threshold value as a function of that threshold value.

* * * * *